United States Patent
Takayanagi et al.

(10) Patent No.: US 12,171,541 B2
(45) Date of Patent: Dec. 24, 2024

(54) MAGNETIC RESONANCE IMAGING APPARATUS, HYPERPOLARIZATION SIGNAL OBTAINING METHOD, AND NON-VOLATILE COMPUTER-READABLE STORAGE MEDIUM STORING THEREIN HYPERPOLARIZATION SIGNAL OBTAINING PROGRAM

(71) Applicant: CANON MEDICAL SYSTEMS CORPORATION, Otawara (JP)

(72) Inventors: Ryohei Takayanagi, Otawara (JP); Takaya Mori, Nasushiobara (JP); Kagami Fujita, Otawara (JP); Akihiro Taguchi, Sakura (JP); Masao Yui, Otawara (JP)

(73) Assignee: CANON MEDICAL SYSTEMS CORPORATION, Otawara (JP)

( * ) Notice: Subject to any disclaimer, the term of this patent is extended or adjusted under 35 U.S.C. 154(b) by 143 days.

(21) Appl. No.: 18/165,961

(22) Filed: Feb. 8, 2023

(65) Prior Publication Data
US 2023/0255507 A1    Aug. 17, 2023

(30) Foreign Application Priority Data

Feb. 14, 2022    (JP) .................................. 2022-020436

(51) Int. Cl.
*A61B 5/055*    (2006.01)
*A61B 5/00*    (2006.01)

(52) U.S. Cl.
CPC ................ *A61B 5/055* (2013.01); *A61B 5/72* (2013.01)

(58) Field of Classification Search
CPC .................................. A61B 5/055; A61B 5/72
See application file for complete search history.

(56) References Cited

U.S. PATENT DOCUMENTS

| 8,604,787 B2* | 12/2013 | Posse ................. | G01R 33/5676 |
| | | | 324/309 |
| 10,605,883 B2* | 3/2020 | Geraghty ........... | G01R 33/5616 |
| 2008/0116890 A1* | 5/2008 | Hurd .................. | G01R 33/4608 |
| | | | 600/420 |
| 2018/0149717 A1 | 5/2018 | Jelezko et al. | |

FOREIGN PATENT DOCUMENTS

JP    2018-514795 A    6/2018

* cited by examiner

*Primary Examiner* — Gregory H Curran
(74) *Attorney, Agent, or Firm* — Oblon, McClelland, Maier & Neustadt, L.L.P.

(57) ABSTRACT

A magnetic resonance imaging apparatus includes sequence controlling circuitry configured: to obtain, during a time period after excitation of a first nuclide in a hyperpolarized state but no later than before obtainment of a first magnetic resonance signal from the first nuclide, a second magnetic resonance signal from a second nuclide that is different from the first nuclide and is in a non-hyperpolarized state, by exciting the second nuclide; and to control each of gradient magnetic field waveforms so as to cause both a first sum indicating a sum of application amounts of a gradient magnetic field related to the excitation of the second nuclide and a second sum indicating a sum of application amounts of a gradient magnetic field related to the obtainment of the second magnetic resonance signal to be close to zero, no later than before the obtainment of the first magnetic resonance signal.

14 Claims, 6 Drawing Sheets

MAGNETIC RESONANCE IMAGING APPARATUS, HYPERPOLARIZATION SIGNAL OBTAINING METHOD, AND NON-VOLATILE COMPUTER-READABLE STORAGE MEDIUM STORING THEREIN HYPERPOLARIZATION SIGNAL OBTAINING PROGRAM

CROSS-REFERENCE TO RELATED APPLICATIONS

This application is based upon and claims the benefit of priority from Japanese Patent Application No. 2022-020436, filed on Feb. 14, 2022, the entire contents of which are incorporated herein by reference.

FIELD

Embodiments described herein relate generally to a magnetic resonance imaging apparatus, a hyperpolarization signal obtaining method, and a non-volatile computer-readable storage medium storing therein a hyperpolarization signal obtaining program.

BACKGROUND

Conventionally, Magnetic Resonance Imaging (hereinafter, "MRI") apparatuses may be configured to obtain a Magnetic Resonance signal (hereinafter, "MR signal") from a nuclide (or "probe") in a hyperpolarized state. The hyperpolarized state denotes a state in which a distribution of the number of spins occupying an energy level of nuclear spins of atomic nuclei corresponding to an orientation state with respect to a static magnetic field is extremely polarized in comparison to a distribution thereof in a thermal equilibrium (a Boltzmann distribution). An imaging method (which may be referred to as "hyperpolarization MRI") based on an MR signal (hereinafter, "hyperpolarization signal") from a nuclide in a hyperpolarized state is a molecular imaging method that makes it possible to obtain dynamic metabolism information or a physiological process.

The hyperpolarization signal drastically increases in comparison to an MR signal from a nuclide in a non-hyperpolarized state. However, the hyperpolarization signal attenuates with a speed dependent on T1 (spin-grid relaxation time) of the nuclide in the hyperpolarized state. Further, due to impacts of pulsation and/or respiratory movements of an examined subject, if the obtainment position of a hyperpolarization signal has a displacement in excess of a spatial resolution related to the obtainment of the hyperpolarization signal, a problem may arise where reliability of the metabolism information obtained on the basis of the hyperpolarization signal is degraded.

DETAILED DESCRIPTION

A magnetic resonance imaging apparatus according to an embodiment includes sequence controlling circuitry. The sequence controlling circuitry is configured to obtain, during a time period after excitation of a first nuclide in a hyperpolarized state but no later than before obtainment of a first magnetic resonance signal from the first nuclide, a second magnetic resonance signal from a second nuclide that is different from the first nuclide and is in a non-hyperpolarized state, by exciting the second nuclide. The sequence controlling circuitry is configured to control each of gradient magnetic field waveforms so as to cause both a first sum indicating a sum of application amounts of a gradient magnetic field related to the excitation of the second nuclide and a second sum indicating a sum of application amounts of a gradient magnetic field related to the obtainment of the second magnetic resonance signal to be close to zero, no later than before the obtainment of the first magnetic resonance signal.

Exemplary embodiments of a Magnetic Resonance Imaging (hereinafter, "MRI") apparatus, a hyperpolarization signal obtaining method, and a hyperpolarization signal obtaining program will be explained below, with reference to the accompanying drawings. Technical concept of the present embodiment may be adopted for other apparatuses such as a sequencer (a sequence controlling apparatus) configured to control an MRI apparatus or to any of various types of modalities each combined with an MRI apparatus, such as a Positron Emission Tomography (PET)-MRI apparatus or a Single Photon Emission Computed Tomography (SPECT)-MRI apparatus.

EMBODIMENTS

Figure 1:
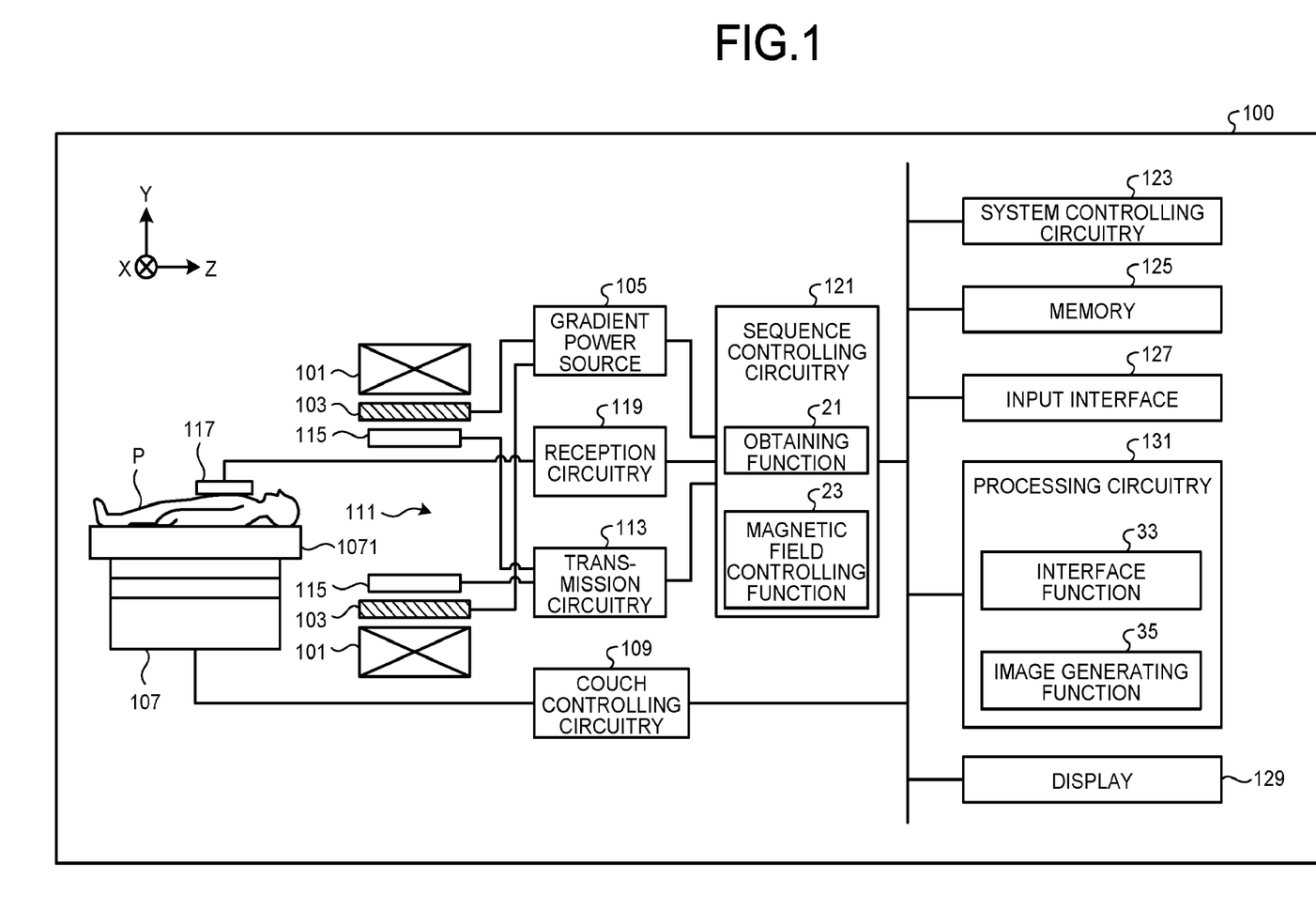
FIG. 1 is a block diagram illustrating an example of a magnetic resonance imaging apparatus according to an embodiment.

FIG. 1 is a diagram illustrating an example of an MRI apparatus 100 according to an embodiment of the present disclosure. As illustrated in FIG. 1, the MRI apparatus 100 includes a static magnetic field magnet 101, a gradient coil 103, a gradient power source 105, a couch 107, couch controlling circuitry 109, transmission circuitry 113, a transmission coil 115, a reception coil 117, reception circuitry 119, sequence controlling circuitry (which may be referred to as imaging controlling circuitry or an imaging controlling unit) 121, system controlling circuitry (a system controlling unit) 123, a memory 125, an input interface 127, a display 129, and processing circuitry 131.

The static magnetic field magnet 101 is a magnet formed to have a hollow and substantially circular cylindrical shape. The static magnetic field magnet 101 is configured to generate a substantially uniform static magnetic field in the space inside thereof. For example, a superconductive magnet or the like may be used as the static magnetic field magnet 101.

The gradient coil 103 is a coil formed to have a hollow and substantially circular cylindrical shape and is arranged on the inner surface side of a circular cylindrical cooling container. By individually receiving electric current supplies from the gradient power source 105, the gradient coil 103 is configured to generate gradient magnetic fields of which magnetic field intensities change along X-, Y-, and Z-axes that are orthogonal to one another. The gradient magnetic fields generated along the X-, Y-, and Z-axes by the gradient coil 103 form, for example, a slice selecting gradient magnetic field, a phase encoding gradient magnetic field, and a frequency encoding gradient magnetic field. The slice selecting gradient magnetic field is used for arbitrarily determining an imaged cross-sectional plane. The phase encoding gradient magnetic field is used for changing the phase of a magnetic resonance signal (hereinafter, "MR signal") in accordance with spatial positions. The frequency encoding gradient magnetic field is used for changing the frequency of an MR signal in accordance with spatial positions.

The gradient power source 105 is a power source apparatus configured to supply the electric currents to the gradient coil 103 under control of the sequence controlling circuitry 121.

The couch 107 is an apparatus provided with a couchtop 1071 on which an examined subject (hereinafter, "patient") P is placed. The couch 107 is configured to insert the couchtop 1071 on which the patient P is placed, into a bore 111, under control of the couch controlling circuitry 109.

The couch controlling circuitry 109 is circuitry configured to control the couch 107. The couch controlling circuitry 109 is configured to move the couchtop 1071 in longitudinal directions and up-and-down directions, as well as left-and-right directions in some situations, by driving the couch 107 according to instructions received from an operator via the input/output interface 127.

The transmission circuitry 113 is configured to supply a radio frequency pulse modulated with a Larmor frequency to the transmission coil 115, under control of the sequence controlling circuitry 121. For example, the transmission circuitry 113 includes an oscillating unit, a phase selecting unit, a frequency converting unit, an amplitude modulating unit, a Radio Frequency (RF) amplifier, and the like. The oscillating unit is configured to generate an RF pulse at a resonance frequency unique to targeted atomic nuclei placed in the static magnetic field. The phase selecting unit is configured to select a phase of the RF pulse generated by the oscillating unit. The frequency converting unit is configured to convert the frequency of the RF pulse output from the phase selecting unit. The amplitude modulating unit is configured to modulate the amplitude of the RF pulse output from the frequency converting unit, according to a sinc function, for example. The RF amplifier is configured to amplify the RF pulse output from the amplitude modulating unit and to supply the amplified RF pulse to the transmission coil 115.

The transmission coil 115 is an RF coil arranged on the inside of the gradient coil 103. The transmission coil 115 is configured to generate an RF pulse corresponding to a radio frequency magnetic field in accordance with the output of the transmission circuitry 113.

The reception coil 117 is an RF coil arranged on the inside of the gradient coil 103. The reception coil 117 is configured to receive an MR signal emitted from the patient P, due to the radio frequency magnetic field. The reception coil 117 is configured to output the received MR signal to the reception circuitry 119. For example, the reception coil 117 is a coil array including one or more (typically two or more) coil elements (hereinafter, "the plurality of coils"). In the following sections, to explain a specific example, it will be assumed that the reception coil 117 is a coil array including the plurality of coils.

Further, although FIG. 1 illustrates the example in which the transmission coil 115 and the reception coil 117 are separate RF coils, the transmission coil 115 and the reception coil 117 may be embodied as an integrally-formed transmission/reception coil. The transmission/reception coil corresponds to an imaged site of the patient P and is a local transmission/reception RF coil such as a head coil, for example.

Under control of the sequence controlling circuitry 121, the reception circuitry 119 is configured to generate a digital MR signal (hereinafter, "MR data") on the basis of the MR signal output from the reception coil 117. More specifically, the reception circuitry 119 is configured to generate the MR data, by performing signal processing processes (e.g., wave detection, filtering, etc.) on the MR signal output from the reception coil 117 and subsequently performing an Analog-to-Digital conversion (hereinafter, "A/D conversion") on the data resulting from the signal processing processes. The reception circuitry 119 is configured to output the generated MR data to the sequence controlling circuitry 121. For example, the MR data is generated for each of the plurality of coils and is output to the sequence controlling circuitry 121 together with a tag identifying the corresponding one of the plurality of coils.

The sequence controlling circuitry 121 is configured to perform an imaging process on the patient P, by controlling the gradient power source 105, the transmission circuitry 113, the reception circuitry 119, and the like, according to an image taking protocol output from the processing circuitry 131. The image taking protocol includes a pulse sequence corresponding to the type of a medical examination. The image taking protocol defines: a magnitude of the electric current to be supplied by the gradient power source 105 to the gradient coil 103; timing with which the electric current is to be supplied by the gradient power source 105 to the gradient coil 103; a magnitude and a time width of the radio frequency pulse to be supplied by the transmission circuitry 113 to the transmission coil 115; timing with which the radio frequency pulse is to be supplied by the transmission circuitry 113 to the transmission coil 115; timing with which the MR signal is to be received by the reception coil 117; and the like. When having received the MR data from the reception circuitry 119, as a result of imaging the patient P by driving the gradient power source 105, the transmission circuitry 113, the reception circuitry 119, and the like, the sequence controlling circuitry 121 is configured to transfer the received MR data to the processing circuitry 131.

In the following sections, to explain a specific example, it is assumed that the pulse sequence executed by the sequence controlling circuitry 121 is a pulse sequence (hereinafter, "hyperpolarization navigator sequence") for obtaining a hyperpolarization signal generated from a first nuclide in a hyperpolarized state and a navigator echo for detecting body movements of the patient P. The hyperpolarized state denotes a state in which a distribution of the number of spins occupying an energy level of nuclear spins of atomic nuclei corresponding to an orientation state with respect to a static magnetic field is extremely polarized in comparison to a distribution thereof in a thermal equilibrium (a Boltzmann distribution). The hyperpolarization navigator sequence is a pulse sequence for obtaining, for example, a first magnetic resonance signal (hereinafter, "hyperpolarization signal") related to metabolism information of the patient P from the first nuclide in the hyperpolarized state (hereinafter, "hyperpolarized nuclide") and obtaining a second magnetic resonance signal (hereinafter, "navigator echo") from protons by exciting a second nuclide in the patient, during the time period after excitation of the hyperpolarized nuclide in the hyperpolarized state, but no later than before the obtainment of the hyperpolarization signal. The second nuclide may be the protons (hydrogen atoms), for example. In the following sections, to explain a specific example, it will be assumed that the second nuclide is the protons. The hyperpolarization navigator sequence will be explained in detail later.

It will be assumed that the hyperpolarized nuclide is $^{13}C$ which is an isotope of Carbon $^{12}C$, for example. However, the hyperpolarized nuclide does not necessarily have to be $^{13}C$ and may be selected as appropriate in accordance with the purpose of a medical examination performed for the patient P. The hyperpolarized nuclide is generated by a known hyperpolarization apparatus and is injected into the patient P, before the hyperpolarization navigator sequence is executed, or the like. Further, to explain a specific example, it is assumed that the hyperpolarization navigator sequence for obtaining the hyperpolarization signal by using $^{13}C$ as the hyperpolarized nuclide includes a sequence related to Magnetic Resonance Spectroscopy (MRS) for obtaining metabolism information of the patient P in a non-invasive manner by using $^{13}C$. In the hyperpolarization navigator sequence, the pulse sequence for obtaining the hyperpolarization signal is assumed to be based on a double spin echo scheme and will be briefly explained.

However, in the hyperpolarization navigator sequence, the pulse sequence for obtaining the hyperpolarization signal does not necessarily have to be based on a double spin echo scheme and may be any type of pulse sequence as long as it is possible to obtain a hyperpolarization signal. Further, in the hyperpolarization navigator sequence, to the sequence for obtaining the navigator echo (hereinafter, "navigator sequence"), it is possible to adopt an arbitrary known scheme, such as a spin echo scheme, a field echo scheme (a gradient echo scheme), or a pencil beam scheme. In the following sections, to explain a specific example, it will be assumed that the navigator sequence is based on a field echo scheme.

As hardware resources thereof, the sequence controlling circuitry 121 includes a processor, as well as a memory element or the like such as a Read-Only Memory (ROM), a Random Access Memory (RAM), and/or the like. The term "processor" denotes, for example, a Central Processing Unit (CPU), a Micro Processing Unit (MPU), Graphics Processing Unit (GPU), or circuitry such as an Application Specific Integrated Circuit (ASIC) or a programmable logic device (e.g., a Simple Programmable Logic Device (SPLD), a Complex Programmable Logic Device (CPLD), or a Field Programmable Gate Array (FPGA)). The sequence controlling circuitry 121 corresponds to a sequence controlling unit.

The sequence controlling circuitry 121 is configured to read a program related to an obtaining function 21 and a magnetic field controlling function 23, from either a memory installed therein or the memory 125 (explained later). According to the read program, the sequence controlling circuitry 121 is configured to control the transmission circuitry 113 and the gradient power source 105. With this configuration, the sequence controlling circuitry 121 is configured to execute the hyperpolarization navigator sequence.

The sequence controlling circuitry 121 (or a processor) realizing the obtaining function 21 is configured to excite the protons and to obtain the navigator echo from the protons, during the time period after the excitation of the hyperpolarized nuclide in the hyperpolarized state, but no later than before the obtainment of the hyperpolarization signal from the hyperpolarized nuclide. In order to apply a plurality of RF pulses to the hyperpolarized nuclide, the obtaining function 21 is configured to control the transmission circuitry 113. The RF pulses applied to the hyperpolarized nuclide include, for example, a flip pulse (or "excitation pulse") for exciting the hyperpolarized nuclide and a plurality of flop pulses (or "refocus pulses") for causing spin of the hyperpolarized nuclide to re-converge.

For example, the obtaining function 21 is configured to excite the protons and to obtain the navigator echo, in the time period between two adjacent flop pulses among the plurality of flop pulses. More specifically, the obtaining function 21 is configured to excite the protons and to obtain the navigator echo, in the time period between two applications of a gradient magnetic field related to the application of the plurality of flop pulses. Even more specifically, the obtaining function 21 is configured to obtain the hyperpolarization signal after one of the plurality of flop pulses that is applied after the obtainment of the navigator echo. The sequence controlling circuitry 121 realizing the obtaining function 21 corresponds to an obtaining unit.

The sequence controlling circuitry 121 (or a processor) realizing the magnetic field controlling function 23 is configured, no later than before the obtainment of the hyperpolarization signal, to cause both a first sum and a second sum to be close to zero, the first sum being a sum of application amounts of the gradient magnetic field related to the excitation of the protons and the second sum being a sum of application amounts of the gradient magnetic field related to the obtainment (acquisition) of the navigator echo. The application amounts of the gradient magnetic field corresponds to a value obtained by integrating intensities of the gradient magnetic field over the application period of the gradient magnetic field. In other words, the first sum corresponds to a value obtained as a result of calculating a value (which may be called "gradient moment") by integrating the intensities of the gradient magnetic field related to the excitation of the protons over the time period during which the gradient magnetic field is applied in relation to the excitation of the protons and further adding together the calculated values from a certain number of sessions at each of which the gradient magnetic field is applied in relation to the excitation of the protons. Further, the second sum corresponds to a value obtained as a result of calculating a value by integrating the intensities of the gradient magnetic field related to the obtainment (acquisition) of the navigator echo over the time period during which the gradient magnetic field is applied in relation to the obtainment of the navigator echo and further adding together the calculated values from a certain number of sessions at each of which the gradient magnetic field is applied in relation to the obtainment of the navigator echo.

In other words, the magnetic field controlling function 23 is configured to control the gradient power source 105 so as to cause both the first sum and the second sum to be close to zero, no later than before the obtainment of the hyperpolarization signal. Because the intensities of the gradient magnetic field in the first sum and the second sum is set in advance, in accordance with the image taking protocol, the magnetic field controlling function 23 is configured to control the application time periods of the gradient magnetic field in the first sum and the second sum, for instance. In an example, the magnetic field controlling function 23 may be configured to control the gradient power source 105, so as to cause the first sum and the second sum to be close to zero, no later than before the application of the last one of the plurality of flop pulses. Preferably, the first sum and the second sum are both zero. In that situation, the magnetic field controlling function 23 is configured to control the gradient power source 105 so as to make both the first sum and the second sum zero. The sequence controlling circuitry 121 realizing the magnetic field controlling function 23 corresponds to a magnetic field controlling unit.

As hardware resources thereof, the system controlling circuitry 123 includes a processor, as well as a memory element or the like such as a ROM, a RAM, and/or the like and is configured to control the MRI apparatus 100 by employing a system controlling function. More specifically, the system controlling circuitry 123 is configured to read a system controlling program stored in a memory, to load the read program into the memory, and to control pieces of circuitry in the MRI apparatus 100 according to the loaded system controlling program.

For example, the system controlling circuitry 123 is configured to read the image taking protocol from the memory 125, on the basis of an image taking condition input by the operator via the input interface 127. The system controlling circuitry 123 is configured to transmit the image taking protocol to the sequence controlling circuitry 121 and to control the imaging process performed on the patient P. The system controlling circuitry 123 is realized by using a processor, for example. Alternatively, the system controlling circuitry 123 may be incorporated in the processing circuitry 131. In that situation, the system controlling function is executed by the processing circuitry 131, so that the processing circuitry 131 functions as a substitute of the system controlling circuitry 123. Because the description of the processor realizing the system controlling circuitry 123 is the same as that presented above, explanations thereof will be omitted.

The memory 125 is configured to store therein various types of programs related to the system controlling function executed by the system controlling circuitry 123, various types of image taking protocols, image taking conditions including a plurality of image taking parameters defining the image taking protocols, and the like. Further, the memory 125 is configured to store therein the obtaining function 21 and the magnetic field controlling function 23 realized by the sequence controlling circuitry 121, as well as an interface function 33 and an image generating function 35 realized by the processing circuitry 131, in the form of computer-executable programs.

Further, the memory 125 is configured to store therein various types of data obtained by the obtaining function 21, various types of data used for processes performed by the image generating function 35, MR images generated by the image generating function 35, and the like. Also, the memory 125 is configured to store therein: MR data obtained as a result of a scan performed on the patient P; and an algorithm for reconstructing an MR image on the basis of the MR data.

Furthermore, the memory 125 may be configured to store therein various types of data received via a communication interface (not illustrated). For example, the memory 125 may store therein information (an imaged site, the purpose of a medical examination, etc.) related to an examination order for the patient P received from an information processing system such as a Radiology Information System (RIS) provided in a medical institution.

For example, the memory 125 may be realized by using a semiconductor memory element such as a ROM, a RAM, or a flash memory, or a Hard Disk Drive (HDD), a Solid State Drive (SSD), an optical disc, or the like. Alternatively, the memory 125 may be realized by using a Compact Disc Read-Only Memory (CD-ROM) drive, a Digital Versatile Disc (DVD) drive, a drive apparatus configured to read and write various types of information from and to a portable storage medium such as a flash memory, or the like.

The input interface 127 is configured to receive various types of instructions and inputs of information from the operator. For example, the input interface 127 is realized by using a trackball, a switch button, a mouse, a keyboard, a touchpad on which input operations can be performed by touching an operation surface thereof, a touch screen in which a display screen and a touchpad are integrally formed, contactless input circuitry using an optical sensor, audio input circuitry, and/or the like. The input interface 127 is connected to the processing circuitry 131 and is configured to convert the input operations received from the operator into electrical signals and to output the electrical signals to the processing circuitry 131.

In the present disclosure, the input interface 127 does not necessarily have to include physical operation component parts such as a mouse, a keyboard, and/or the like. For example, possible examples of the input interface 127 include electrical signal processing circuitry configured to receive an electrical signal corresponding to an input operation from an external input device provided separately from the MRI apparatus 100 and to output the electrical signal to controlling circuitry or the like.

According to a user instruction, the input interface 127 is configured to receive an input a Field Of View (FOV) with respect to a pre-scan image displayed on the display 129. More specifically, according to a range setting instruction from the user, the input interface 127 is configured to receive the input of the FOV within a locator image displayed on the display 129. Further, according to a user instruction based on an examination order, the input interface 127 is configured to receive inputs of various types of image taking parameters related to scans and an instruction to select a pulse sequence.

Under control of the processing circuitry 131 or the system controlling circuitry 123, the display 129 is configured to display various types of Graphical User Interfaces (GUIs), MR images generated by the processing circuitry 131, and the like. Further, the display 129 is configured to display the image taking parameters related to the scans, various types of information related to image processing, and the like. For example, the display 129 may be realized by a Cathode Ray Tube (CRT) display, a liquid crystal display, an organic Electroluminescence (EL) display, a Light Emitting Diode (LED) display, a plasma display, or any of other arbitrary displays including display mechanisms and monitors that are known in the relevant technical field.

For example, the processing circuitry 131 is realized by using a processor such as that described above, or the like. The processing circuitry 131 includes the interface function 33, the image generating function 35, and the like. The processing circuitry 131 realizing the interface function 33 and the image generating function 35 corresponds to an interface unit and an image generating unit, respectively. The functions such as the interface function 33, the image generating function 35, and the like are stored in the memory 125 in the form of computer-executable programs. For example, the processing circuitry 131 is configured to realize the functions corresponding to the programs, by reading and executing the programs from the memory 125. In other words, the processing circuitry 131 that has read the programs has the functions such as the interface function 33, the image generating function 35, and the like.

In the description above, the example was explained in which the "processor" is configured to read and execute the programs corresponding to the functions from the memory 125; however, possible embodiments are not limited to this example. For instance, when the processor is a CPU, the processor is configured to realize the functions by reading and executing the programs saved in the memory 125. In contrast, when the processor is an ASIC, instead of having the programs saved in the memory 125, the functions are directly incorporated in the circuitry of the processor as logic circuitry. Further, the processors of the present embodiments do not each necessarily have to be structured as a single piece of circuitry. It is also acceptable to structure one processor by combining together a plurality of pieces of independent circuitry, so as to realize the functions thereof. Further, although the example was explained in which the single piece of storage circuitry is configured to store therein the programs corresponding to the processing functions, it is also acceptable to provide a plurality of pieces of storage circuitry in a distributed manner, so that the processing circuitry 131 reads a corresponding program from each of the individual pieces of storage circuitry.

By employing the interface function 33, the processing circuitry 131 is configured to transmit information about the hyperpolarization navigator sequence to the sequence controlling circuitry 121 and to receive MR data (hereinafter, "hyperpolarization data") about the hyperpolarization signal from the sequence controlling circuitry 121. Upon receipt of the hyperpolarization data, the interface function 33 is configured to store the received hyperpolarization data into the memory 125. Further, upon receipt of MR data (hereinafter, "navigator data") related to the navigator echo from the sequence controlling circuitry 121, the interface function 33 is configured to store the navigator data into the memory 125.

By employing the image generating function 35, the processing circuitry 131 is configured to generate an image (hereinafter, "hyperpolarization image") related to metabolism of the hyperpolarized nuclide, by performing a body movement correction on the hyperpolarization data while using the navigator data. The body movement correction on the hyperpolarization data associated with body movements of the patient P is carried out by using the navigator data. Because it is possible to use, as appropriate, any of various types of known methods for the body movement correction in the hyperpolarization data, explanations thereof will be omitted.

Figure 2:
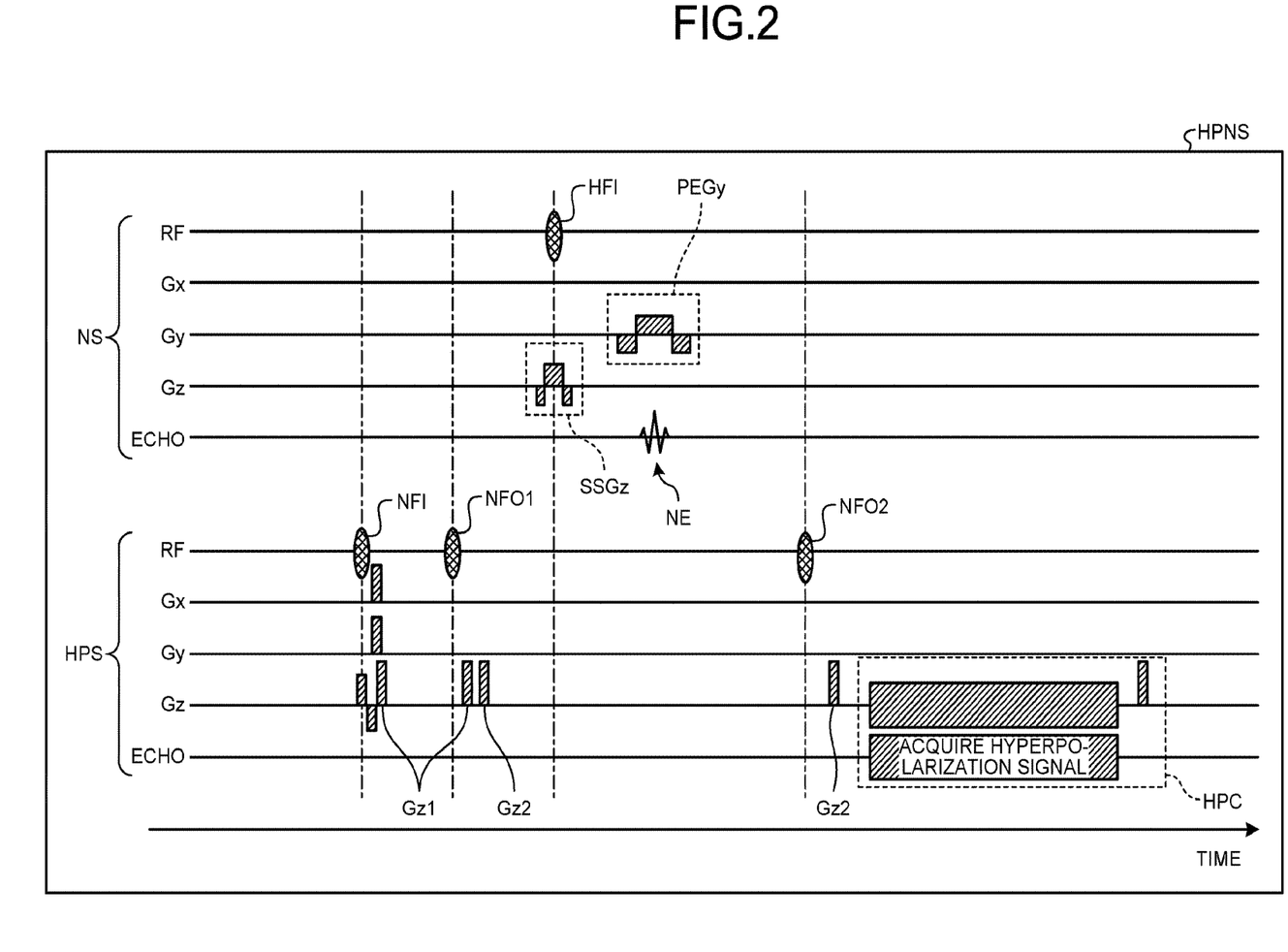
FIG. 2 is a chart according to the embodiment illustrating an example of a hyperpolarization navigator sequence related to excitation of a hyperpolarized nuclide in one session.

FIG. 2 is a chart illustrating an example of a hyperpolarization navigator sequence HPNS related to the excitation of a hyperpolarized nuclide in one session. FIG. 2 is not an exact sequence chart, but is a schematic chart. In FIG. 2, for the sake of convenience in the explanation, the hyperpolarization navigator sequence HPNS is indicated as being separated into a navigator sequence NS and a sequence (hereinafter, "hyperpolarization sequence") HPS related to the obtainment (the acquisition) of the hyperpolarization signal. In other words, in the actual hyperpolarization navigator sequence HPNS, the RF pulses, the gradient magnetic fields (Gx, Gy, and Gz), and an echo signal (hereinafter, "acquisition echo") for the hyperpolarized nuclide related to the navigator sequence NS and to the hyperpolarization sequence HPS are arranged on mutually the same axis.

As illustrated in FIG. 2, for the RF pulses, the gradient magnetic fields (Gx, Gy, and Gz), and the acquisition echo for the echo signal, the plurality of horizontal axes along the time axis each indicate an intensity of "0". The region above each of the plurality of horizontal axes corresponds to a region having positive intensities, whereas the region below each of the plurality of horizontal axes corresponds to a region having negative intensities.

As illustrated in FIG. 2, in the hyperpolarization sequence HPS, the RF pulses include one flip pulse NFI and two flop pulses (NFO1 and NFO2). In the following sections, for the sake of convenience in the explanation, of the two flop pulses (NFO1 and NFO2), the flop pulse applied to the patient P at an earlier time will be referred to as an earlier flop pulse NFO1. Further, of the two flop pulses (NFO1 and NFO2), the flop pulse applied to the patient P at a later time will be referred to as a later flop pulse NFO2.

In the hyperpolarization sequence HPS illustrated in FIG. 2, under the control of the sequence controlling circuitry 121, the slice selecting gradient magnetic field Gz is applied to the patient P, together with the flip pulse NFI. After the application of the flip pulse NFI, the phase encoding gradient magnetic field Gy and the frequency encoding gradient magnetic field Gx are applied to the patient P, under the control of the sequence controlling circuitry 121.

As illustrated in FIG. 2, according to the double spin echo scheme, as for the RF pulses, after the flip pulse NFI, the earlier flop pulse NFO1 and the later flop pulse NFO2 are applied to the patient P. Before and after the earlier flop pulse NFO1 in terms of time, a pair of slice selecting gradient magnetic fields Gz1 are applied to the patient P. Also, before and after the later flop pulse NFO2 in terms of time, a pair of slice selecting gradient magnetic fields Gz2 are applied to the patient P. Of each of the pairs of slice selecting gradient magnetic fields (Gz1 and Gz2), the earlier gradient magnetic field is used for selecting a slice to which the corresponding one of the two flop pulses (NFO1 and NFO2) is applied. Further, of each of the pairs of slice selecting gradient magnetic fields (Gz1 and Gz2), the later gradient magnetic field is used for restoring a spin state changed by the gradient magnetic field applied for selecting the slice, back to an original state.

As illustrated in FIG. 2, after the application of the later slice selecting gradient magnetic field included in the pair of slice selecting gradient magnetic fields Gz2 related to the later flop pulse NFO2, the sequence controlling circuitry 121 is configured to execute an acquisition sequence HPC related to the acquisition of the hyperpolarization signal. According to the double spin echo scheme, the acquisition sequence is carried out according to a flyback readout trajectory, for example. Because it is possible to adopt a known method for the flyback readout trajectory, explanations thereof will be omitted. After the flyback readout trajectory is carried out, the sequence controlling circuitry 121 is configured to control the gradient power source 105 so as to apply a spoiler pulse to the patient P in the acquisition sequence HPC.

As illustrated in FIG. 2, after the application of the earlier slice selecting gradient magnetic field included in the pair of slice selecting gradient magnetic fields Gz1 related to the earlier flop pulse NFO1, the sequence controlling circuitry 121 is configured to control the transmission circuitry 113 so as to apply a flip pulse HFI corresponding to excitation of protons related to a navigator echo NE, to the patient P. At the same time, the sequence controlling circuitry 121 is configured to control the gradient power source 105 so as to generate a slice selecting gradient magnetic field SSGz related to the flip pulse HFI. In addition, the sequence controlling circuitry 121 is configured to control the gradient power source 105, so as to cause a first sum of gradient magnetic field intensities of the slice selecting gradient magnetic field SSGz, i.e., the first sum of the application amounts of the gradient magnetic field related to the excitation of the protons, to be close to zero. Preferably, the sequence controlling circuitry 121 controls the gradient power source 105 so as to make the first sum zero.

Subsequently, as illustrated in FIG. 2, the sequence controlling circuitry 121 is configured to control the gradient power source 105 so as to generate a phase encoding gradient magnetic field PEGy, for example, in relation to the reception of the navigator echo NE. In addition, the sequence controlling circuitry 121 is configured to control the gradient power source 105, so as to cause a second sum of gradient magnetic field intensities of the phase encoding gradient magnetic field PEGy, i.e., the second sum of the application amounts of the gradient magnetic field related to the acquisition of the navigator echo, to be close to zero. Preferably, the sequence controlling circuitry 121 controls the gradient power source 105 so as to make the second sum zero.

As illustrated in FIG. 2, by employing the obtaining function 21, the sequence controlling circuitry 121 is configured to excite the protons and to obtain the navigator echo NE, in the time period between the two flop pulses. In that situation, by employing the magnetic field controlling function 23, the sequence controlling circuitry 121 is configured to control the gradient power source 105 so as to cause both the first sum and the second sum to be close to zero, preferably so as to make both the first sum and the second sum zero. More specifically, by employing the obtaining function 21, the sequence controlling circuitry 121 is configured to control the gradient power source 105 so as to excite the protons and to obtain the navigator echo NE in the time period between the pair of slice selecting gradient magnetic fields Gz2 related to the later flop pulse NFO2. Further, by employing the obtaining function 21, the sequence controlling circuitry 121 is configured to obtain the hyperpolarization signal, after the later flop pulse NFO2 applied after the obtainment of the navigator echo NE.

As illustrated in FIG. 2, the following do not overlap with one another: the application time period of the gradient magnetic field at the time of exciting the hyperpolarized nuclide; the application time period (hereinafter, "hyperpolarization signal acquisition period") of the gradient magnetic field related to the acquisition of the first magnetic resonance signal; the application time period (hereinafter, "proton excitation period") of the gradient magnetic field at the time of exciting the protons; and the application time period (hereinafter, "navigator echo acquisition period") of the gradient magnetic field related to the acquisition of the second magnetic resonance signal. In other words, by employing the magnetic field controlling function 23, the sequence controlling circuitry 121 is configured, as illustrated in FIG. 2, to control the gradient power source 105 so as to cause both the first sum and the second sum to be close to (equal to) zero, while the proton excitation period, the hyperpolarization signal acquisition period, and the navigator echo acquisition period do not overlap with one another.

Furthermore, after the execution of the acquisition sequence HPC, i.e., after the obtainment of the hyperpolarization signal, the sequence controlling circuitry 121 may be configured to control the gradient power source 105 so as to generate a spoiler pulse related to the navigator echo NE or the like. In that situation, after the obtainment of the hyperpolarization signal, the obtaining function 21 is configured to generate the spoiler pulse related to the acquisition of the navigator echo NE.

The MRI apparatus 100 according to the embodiment described above is configured to excite the protons and to obtain the navigator echo NE from the protons during the time period after the application of the flip pulse to the hyperpolarized nuclide but no later than before the execution of the acquisition sequence HPC and configured to cause both the first sum and the second sum to be close to zero no later than before the obtainment of the hyperpolarization signal. Preferably, in the hyperpolarization navigator sequence HPNS, the first sum and the second sum are both zero. More specifically, in the MRI apparatus 100, the plurality of RF pulses applied to the hyperpolarized nuclide include the flip pulse and the two flop pulses. The MRI apparatus 100 is configured to excite protons and to obtain the navigator echo NE in the time period between the two flop pulses.

Further, the MRI apparatus 100 according to the embodiment is configured to excite the protons and to obtain the navigator echo NE, in the time period between the two applications of the gradient magnetic field related to the application of the two flop pulses. Further, the MRI apparatus 100 is configured so that the hyperpolarization signal acquisition period, the proton excitation period, and the navigator echo acquisition period do not overlap with one another. More specifically, the MRI apparatus 100 is configured to obtain the hyperpolarization signal after the application of the later flop pulse NFO2. In this situation, no later than before the application of the later flop pulse NFO2, the MRI apparatus 100 may cause the first sum and the second sum to be close to zero. Further, after the obtainment of the hyperpolarization signal, the MRI apparatus 100 is configured to generate the spoiler pulse related to the acquisition of the navigator echo.

With these configurations, the MRI apparatus 100 according to the embodiment is able to obtain the navigator echo NE by causing both the first sum and the second sum to be close to zero in the time period between the pair of slice selecting gradient magnetic fields Gz2 related to the later flop pulse NFO2. It is therefore possible to obtain the navigator echo NE, while keeping loss of the intensities of the hyperpolarization signal as small as possible. In other words, the MRI apparatus 100 is able to obtain the hyperpolarization signal and the navigator echo NE, without allowing the application of the gradient magnetic field related to the acquisition of the navigator echo NE to contribute as a spoiler to the spin of the hyperpolarized nuclide and without allowing the application of the gradient magnetic field related to the acquisition of the hyperpolarization signal to contribute as a spoiler to the spin of the protons. Consequently, even in the situation where, due to impacts of pulsation and/or respiratory movements, a positional displacement is caused in excess of a spatial resolution related to the obtainment of the hyperpolarization signal, it is possible to improve reliability of the metabolism information in the hyperpolarization image, by carrying out the body movement correction on the hyperpolarization signal while using the navigator echo NE.

In addition, as illustrated in FIG. 2, the MRI apparatus 100 is able to obtain the navigator echo present immediately before the acquisition of the hyperpolarization signal, by performing, in parallel to each other, the excitation of the hyperpolarized nuclide and the obtainment of the navigator echo (the excitation of the protons and the acquisition of the navigator echo). For this reason, the MRI apparatus 100 is able to improve the level of precision of the body movement correction for the patient P carried out on the hyperpolarization data. Further, in the hyperpolarization navigator sequence HPNS of the MRI apparatus 100, although it is necessary to secure the time period (hereinafter, "navigator acquisition period") for incorporating the sequence used for obtaining the navigator echo NE, when a known hyperpolarization signal acquisition signal includes the navigator acquisition period, it is possible to generate a hyperpolarization image having improved reliability of metabolism information, without the need to extend the acquisition time period for the hyperpolarization signal.

First Modification Example

In the present modification example, the navigator echo NE is obtained multiple times, during the time period (hereinafter, "navigator sequence insertion period") after the application of the earlier slice selecting gradient magnetic field included in the pair of slice selecting gradient magnetic fields Gz2 related to the later flop pulse NFO2 but no later than before the application of the later flop pulse NFO2.

Figure 3:
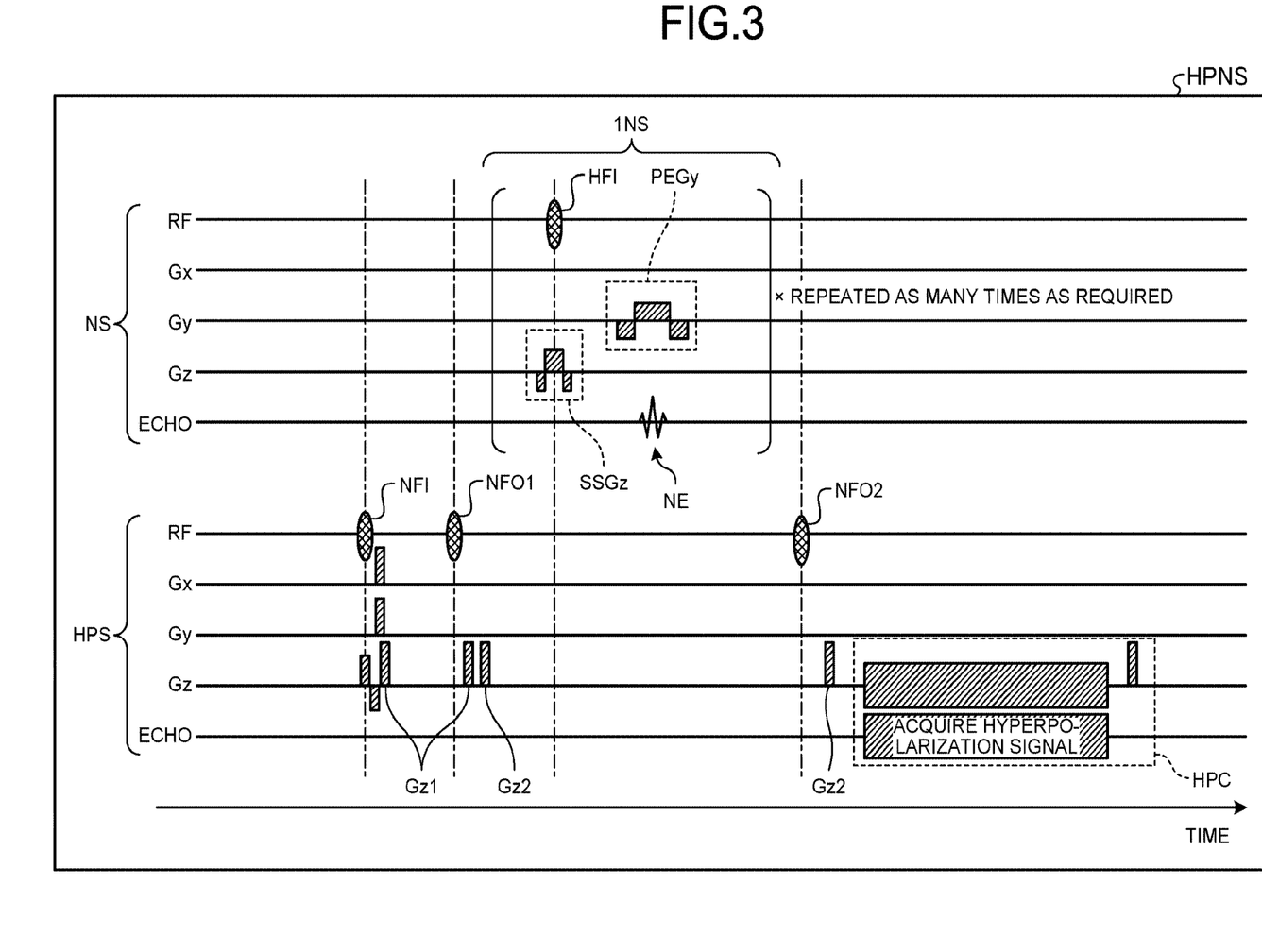
FIG. 3 is a chart illustrating an example of a hyperpolarization navigator sequence according to a first modification example of the embodiment.

FIG. 3 is a chart illustrating an example of a hyperpolarization navigator sequence HPNS according to a first modification example. FIG. 3 is not an exact sequence chart, but is a schematic chart. FIG. 3 indicates that in the navigator sequence NS, a sequence 1NS for obtaining a single navigator echo is repeated a number of times as required. The required number of times is set in advance on the basis of the navigator insertion period and the time required by the sequence 1NS to obtain the single navigator echo. As illustrated in FIG. 3, the MRI apparatus 100 according to the first modification example is configured to obtain a plurality of navigator echoes with respect to the obtainment of the hyperpolarization signal.

The MRI apparatus 100 according to the first modification example is capable of carrying out the body movement correction by using the navigator echo present immediately before the obtainment of the hyperpolarization signal. It is therefore possible to further improve the reliability of the metabolism information in the hyperpolarization image. Because the other advantageous effects of the present modification example are the same as those of the embodiment, explanations thereof will be omitted.

Second Modification Example

In the present modification example, a spin echo scheme is used in a sequence for obtaining the navigator echo in a hyperpolarization navigator sequence HPNS.

Figure 4:
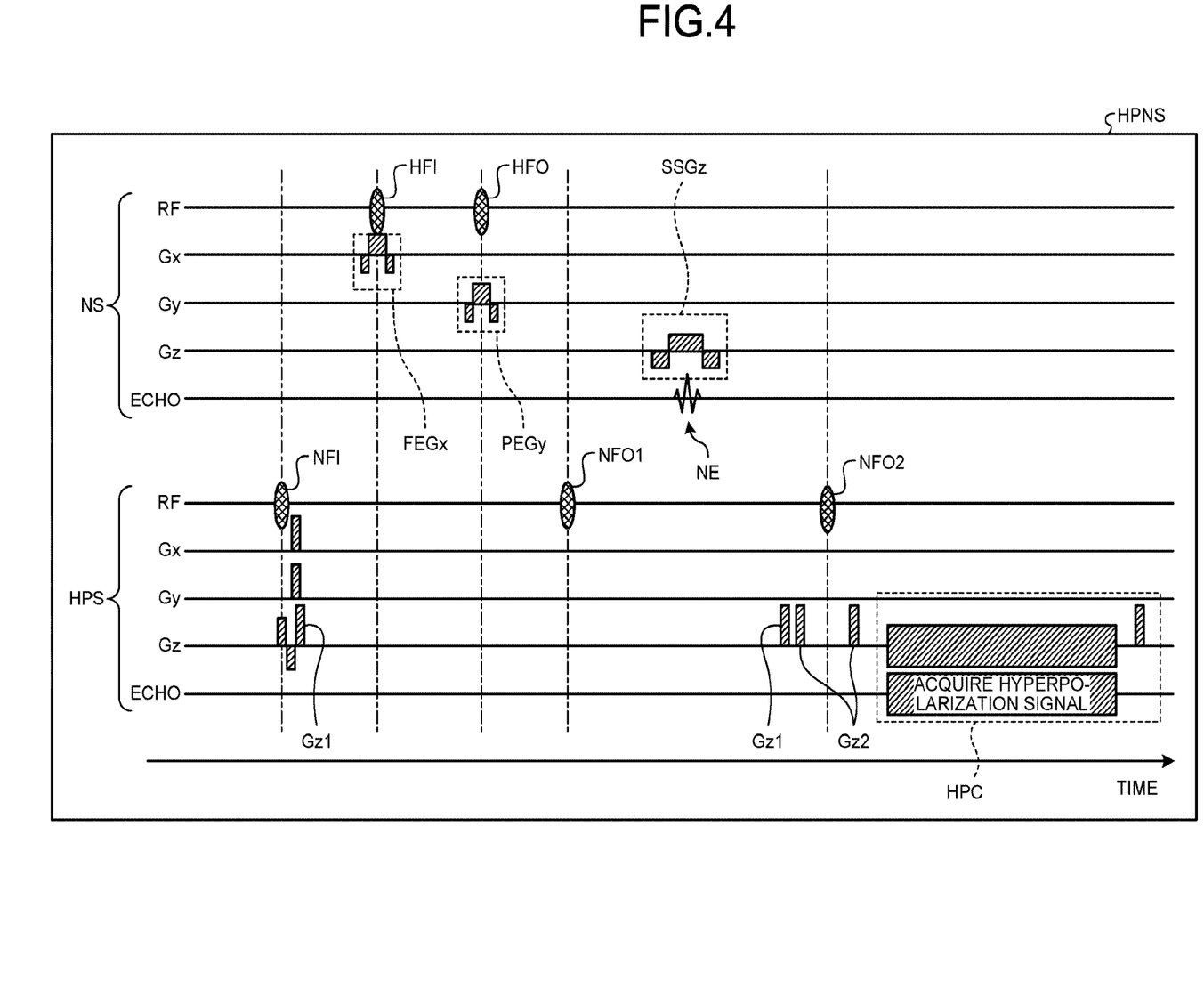
FIG. 4 is a chart illustrating an example of a hyperpolarization navigator sequence according to a second modification example of the embodiment.

FIG. 4 is a chart illustrating an example of the hyperpolarization navigator sequence HPNS according to a second modification example. FIG. 4 is not an exact sequence chart but is a schematic chart. FIG. 4 indicates that, in a navigator sequence NS, RF pulses related to the excitation of the protons is applied during the time period after the application of the flip pulse NFI, but no later than before the application of the flop pulse NFO1. More specifically, the sequence controlling circuitry 121 is configured to control the transmission circuitry 113 so as to apply the flip pulse HFI to the patient P, after the application of the earlier slice selecting gradient magnetic field included in the pair of slice selecting gradient magnetic fields Gz1 related to the earlier flop pulse NFO1. At the same time, the sequence controlling circuitry 121 is configured to control the gradient power source 105 so as to generate a frequency encoding gradient magnetic field FEGx related to the flip pulse HFI, for example.

As illustrated in FIG. 4, the sequence controlling circuitry 121 is configured to control the gradient power source 105 so as to cause a sum of gradient magnetic field intensities of the frequency encode gradient magnetic field FEGx to be close to zero. Preferably, the sequence controlling circuitry 121 controls the gradient power source 105 so as to make the sum zero.

As illustrated in FIG. 4, after the application of the frequency encoding gradient magnetic field FEGx, the sequence controlling circuitry 121 is configured to control the transmission circuitry 113 so as to apply a flop pulse HFO for the protons to the patient P. At the same time, for example, the sequence controlling circuitry 121 is configured to control the gradient power source 105 so as to generate a phase encoding gradient magnetic field PEGy related to the flop pulse HFO. In addition, the sequence controlling circuitry 121 is configured to control the gradient power source 105 so as to cause a sum of gradient magnetic field intensities of the phase encoding gradient magnetic field PEGy to be close to zero.

As illustrated in FIG. 4, by employing the magnetic field controlling function 23, the sequence controlling circuitry 121 is configured to control the gradient power source 105, preferably, so as to make the sum zero. In other words, the sequence controlling circuitry 121 is configured to control the gradient power source 105 so as to cause both of the sum of the gradient magnetic field intensities of the frequency encoding gradient magnetic field FEGx related to the flip pulse HFI for the protons and the sum of the gradient magnetic field intensities of the phase encoding gradient magnetic field PEGy related to the flop pulse HFO for the protons to be zero. The sum of the gradient magnetic field intensities of the frequency encoding gradient magnetic field FEGx related to the flip pulse HFI for the protons and the sum of the gradient magnetic field intensities of the phase encoding gradient magnetic field PEGy related to the flop pulse HFO for the protons correspond to the abovementioned first sum.

As illustrated in FIG. 4, in relation to the reception of the navigator echo NE, the sequence controlling circuitry 121 is configured to control the gradient power source 105 so as to generate a slice selecting gradient magnetic field SSGz, for example. In addition, the sequence controlling circuitry 121 is configured to control the gradient power source 105 so as to cause the second sum of gradient magnetic field intensities of the slice selecting gradient magnetic field SSGz, i.e., the second sum of the application amounts of the gradient magnetic field related to the obtainment of the navigator echo, to be close to zero. Preferably, the sequence controlling circuitry 121 controls the gradient power source 105 so as to make the second sum zero.

In the present modification example, unlike in the embodiment, the protons are excited (by the flip pulse HFI and the flop pulse HFO), during the time period between a time after the application of the earlier slice selecting gradient magnetic field included in the pair of slice selecting gradient magnetic fields Gz1 related to the earlier flop pulse NFO1 and a time before the application of the earlier flop pulse NFO1. Subsequently, the navigator echo NE is obtained during the time period between a time after the application of the earlier flop pulse NFO1 and a time before the application of the later slice selecting gradient magnetic field included in the pair of slice selecting gradient magnetic fields Gz1 related to the earlier flop pulse NFO1. In other words, according to the present modification example, even though the excitation of the protons is different from that in the embodiment, it is possible to obtain the navigator echo NE. Because the other advantageous effects of the present modification example are the same as those of the embodiment, explanations thereof will be omitted.

Third Modification Example

In the present modification example, the sum (the second sum) of the gradient magnetic fields that are simultaneously applied in relation to the obtainment (receipt) of the navigator echo NE is caused to be unbalanced, instead of zero (i.e., The second sum is caused to be non-zero). The hyperpolarized state of a hyperpolarized nuclide transitions into a non-hyperpolarized state, as time elapses since the hyperpolarized state is created. For this reasons, the intensity of the hyperpolarization signal from the hyperpolarized nuclide attenuates as time elapses. The balance between the intensities of the gradient magnetic fields that are simultaneously applied in relation to the obtainment of the navigator echo NE is changed so as to suppress the intensity of the hyperpolarization signal that attenuates over the course of time. For example, by employing the magnetic field controlling function 23, the sequence controlling circuitry 121 is configured to control the gradient power source 105 so as to make the second sum non-zero, so that the attenuation in the intensity of the hyperpolarization signal is inhibited.

Figure 5:
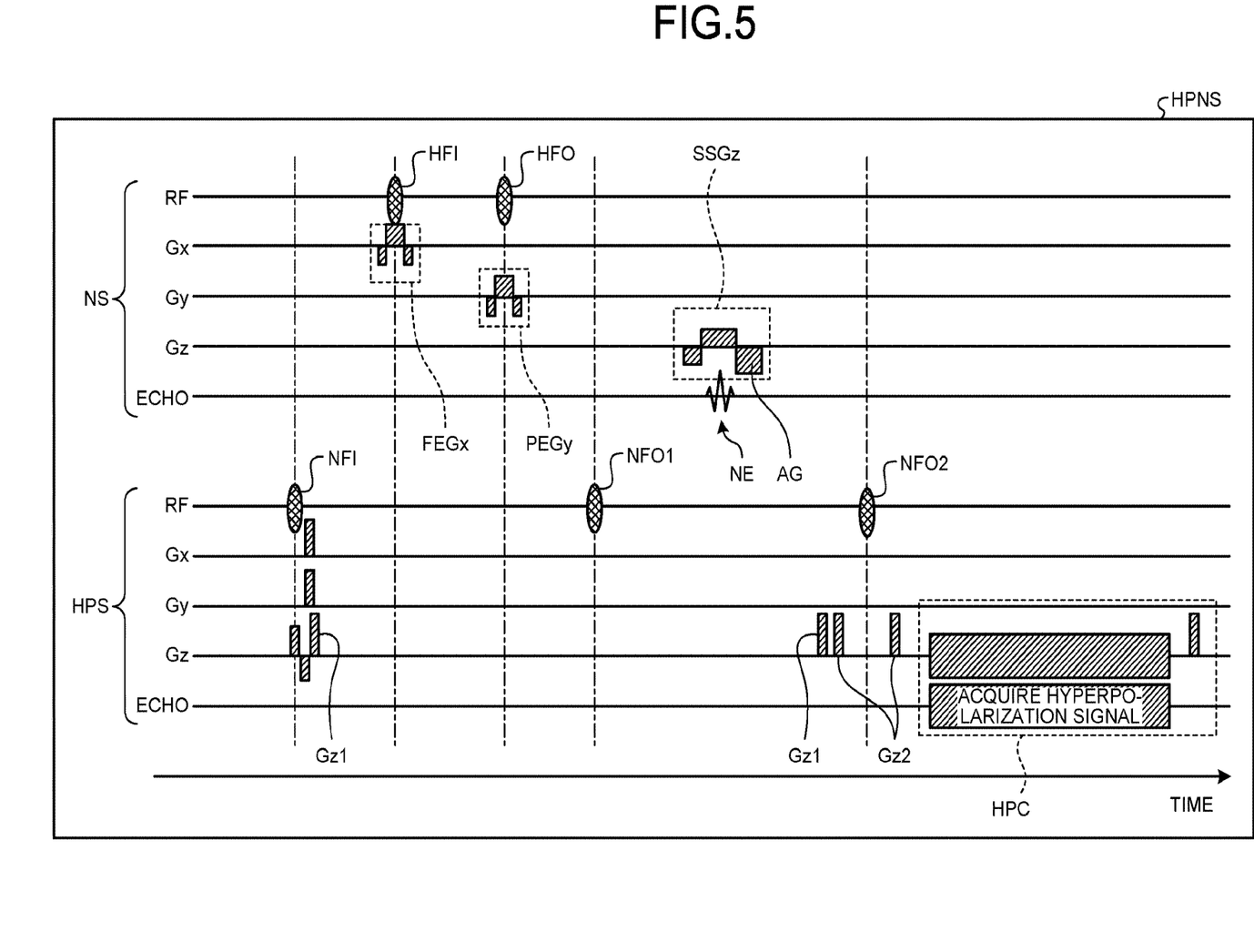
FIG. 5 is a chart according to a third modification example of the embodiment illustrating an example in which balance among slice selecting gradient magnetic fields related to reception of a navigator echo is changed.

FIG. 5 is a chart illustrating an example in which the balance within the slice selecting gradient magnetic field SSGz related to the reception of the navigator echo NE is changed compared to that in FIG. 4. FIG. 5 is not an exact sequence chart but is a schematic chart. As illustrated in FIG. 5, at a later end AG of the slice selecting gradient magnetic field SSGz, the sum of intensities of the slice selecting gradient magnetic field is larger than that in FIG. 4. By employing the magnetic field controlling function 23, for example, the sequence controlling circuitry 121 is configured to adjust the intensity of the gradient magnetic field at the later end AG.

In the present modification with this configuration, it is possible to suppress the intensity of the hyperpolarization signal that attenuates over the course of time. The adjustment of the second sum may be configured as appropriate so as to suppress the intensity of the hyperpolarization signal that attenuates over the course of time. Consequently, according to the present modification example, because it is possible to inhibit the temporal attenuation in the intensity of the hyperpolarization signal, it is possible to further improve the reliability of the metabolism information in the hyperpolarization image. Because the other advantageous effects of the present modification example are the same as those of the embodiment, explanations thereof will be omitted.

Fourth Modification Example

In the present modification example, the flop pulse HFO related to the excitation of the protons and the earlier flop pulse NFO1 related to the hyperpolarized nuclide are applied to the patient P simultaneously in a non-slice selecting manner. For example, when the hyperpolarized nuclide is $^{13}C$, the sequence controlling circuitry 121 is configured, by employing the obtaining function 21, to apply a composite pulse for simultaneously exciting the protons and $^{13}C$, to the patient P, for example. The application of the composite pulse is carried out in the non-slice selecting manner.

Further, the simultaneous excitation of the hyperpolarized nuclide and the protons is not limited to using the composite pulse. It is possible to adopt any of various types of known methods.

Figure 6:
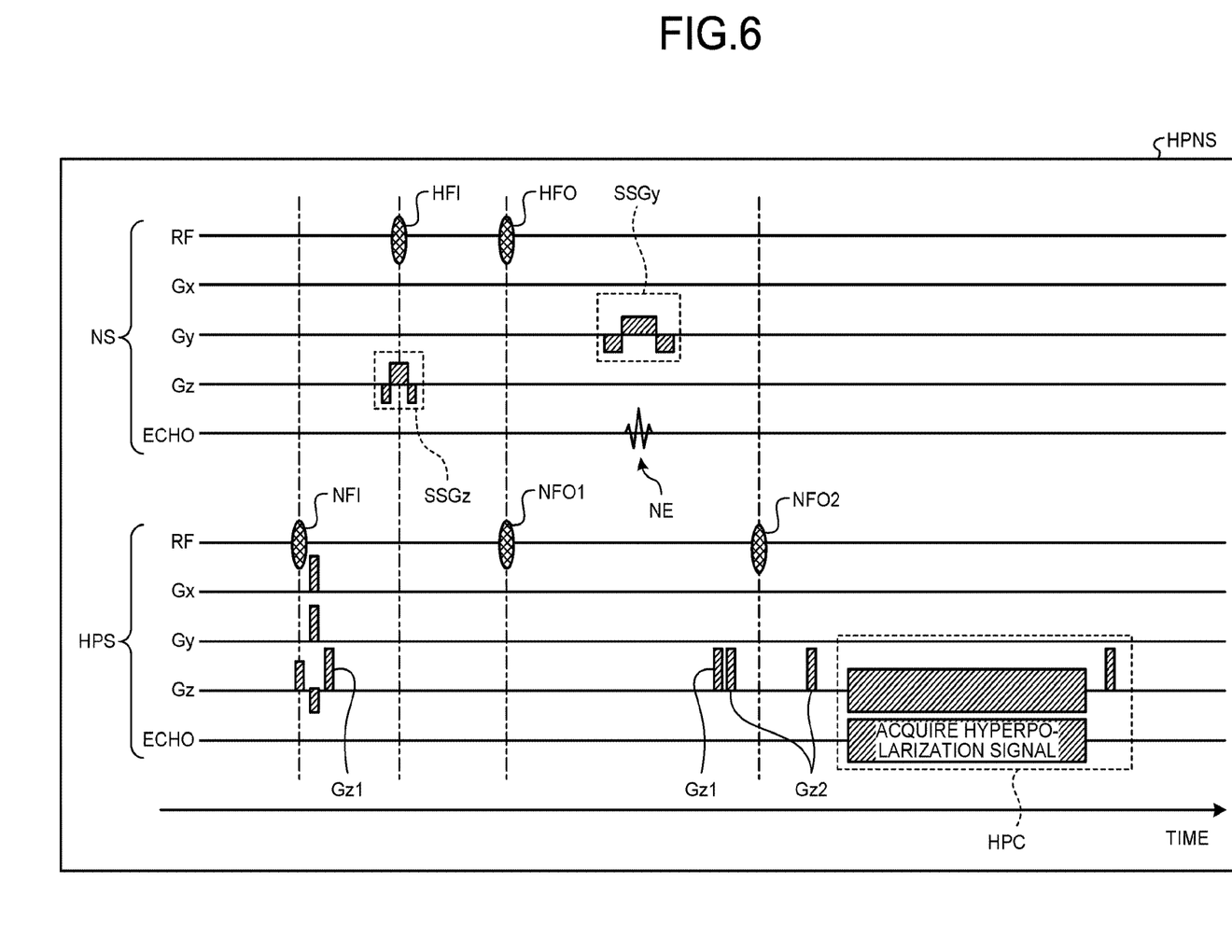
FIG. 6 is a chart according to a fourth modification example of the embodiment illustrating an example of a sequence in which, while a spin echo scheme is used in a navigator sequence, an examined subject P has simultaneously applied thereto a flop pulse for protons and an earlier flop pulse in a non-slice selecting manner.

FIG. 6 is a chart illustrating an example of a sequence in which, while a spin echo scheme is used in the navigator sequence NS, an examined subject P has simultaneously applied thereto the flop pulse HFO for the protons and the earlier flop pulse NFO1, in a non-slice selecting manner. FIG. 6 is not an exact sequence chart but is a schematic chart. As illustrated in FIG. 6, by employing the obtaining function 21, the sequence controlling circuitry 121 is configured to control the transmission circuitry 113 so as to generate the flop pulses related to the protons and to the hyperpolarized nuclide in a simultaneous excitation manner and in the non-slice selecting manner. As a result, the obtaining function 21 is configured to simultaneously carry out the excitation of the hyperpolarized nuclide and the excitation of the protons.

By using the MRI apparatus 100 according to the present modification example, for example, when the spin echo scheme is used for the navigator sequence NS, it is possible to simultaneously apply, to the patient P, the flop pulse HFO for the protons and the earlier flop pulse NFO1 in the non-slice selecting manner. Consequently, the MRI apparatus 100 according to the present modification example is able to shorten the navigator acquisition period, for instance, and is thus able to execute the hyperpolarization navigator sequence HPNS without increasing the imaging time period. Because the other advantageous effects of the present modification example are the same as those of the embodiment, explanations thereof will be omitted.

Further, in the embodiment, the modification examples, and the like described above, the waveforms of the gradient magnetic fields to be controlled by the magnetic field controlling function 23 are explained as being temporally continuous as illustrated in FIGS. 2 to 6; however, possible embodiments are not limited to this example. In other words, the waveforms of the gradient magnetic fields to be controlled may be temporally discontinuous, i.e., temporally separate.

When technical concept according to an aspect of the embodiment is realized as a hyperpolarization signal obtaining method, the hyperpolarization signal obtaining method includes: exciting the first nuclide in the hyperpolarized state; exciting the second nuclide that is different from the first nuclide and is in a non-hyperpolarized state, during the time period no later than before the obtainment of the first magnetic resonance signal (the hyperpolarization signal) from the first nuclide; causing the first sum indicating the sum of the application amounts of the gradient magnetic field related to the excitation of the second nuclide to be close to zero, no later than before the obtainment of the first magnetic resonance signal; obtaining the second magnetic resonance signal (the navigator echo) from the second nuclide; causing the second sum indicating the sum of the application amounts of the gradient magnetic field related to the obtainment of the second magnetic resonance signal to be close to zero, no later than before the obtainment of the first magnetic resonance signal; and obtaining the first magnetic resonance signal after the second sum is caused to be close to zero. Because processing procedures and advantageous effects related to the present hyperpolarization signal obtaining method are the same as those presented in the embodiment, explanations thereof will be omitted.

When technical concept according to an aspect of the embodiment is realized as a hyperpolarization signal obtaining program, the hyperpolarization signal obtaining program causes a computer to realize: controlling the transmission circuitry 113 so as to excite the first nuclide in the hyperpolarized state; controlling the transmission circuitry 113 so as to excite the second nuclide that is different from the first nuclide and is in a non-hyperpolarized state, during the time period no later than before the obtainment of the first magnetic resonance signal (the hyperpolarization signal) from the first nuclide; controlling the gradient power source 105 so as to cause the first sum indicating the sum of the application amounts of the gradient magnetic field related to the excitation of the second nuclide to be close to zero, no later than before the obtainment of the first magnetic resonance signal; controlling the gradient power source 105 so as to obtain the second magnetic resonance signal from the second nuclide; controlling the gradient power source 105 so as to cause the second sum indicating the sum of the application amounts of the gradient magnetic field related to the obtainment of the second magnetic resonance signal to be close to zero, no later than before the obtainment of the first magnetic resonance signal; and controlling the gradient power source 105 so as to obtain the first magnetic resonance signal after the second sum is caused to be close to zero.

For example, it is also possible to realize the hyperpolarization signal obtaining method, by installing the hyperpolarization signal obtaining program in the MRI apparatus 100 or a modality having the MRI apparatus 100 and further loading the program in a memory. In that situation, the program capable of causing the computer to implement the method may be distributed as being stored in a storage medium such as a magnetic disk (e.g., a hard disk), an optical disc (e.g., a CD-ROM, a DVD), or a semiconductor memory. Because procedures and advantageous effects of the processes for obtaining the hyperpolarization signal and the navigator echo realized by the hyperpolarization signal obtaining program are the same as those of the embodiment, explanations thereof will be omitted.

According to at least one aspect of the embodiments and the like described above, it is possible to obtain the data that makes it possible to improve the reliability of the information obtained on the basis of the hyperpolarization signal, while inhibiting the attenuation of the MR signal from the nuclide in the hyperpolarized state.

While certain embodiments have been described, these embodiments have been presented by way of example only, and are not intended to limit the scope of the inventions. Indeed, the novel embodiments described herein may be embodied in a variety of other forms; furthermore, various omissions, substitutions and changes in the form of the embodiments described herein may be made without departing from the spirit of the inventions. The accompanying claims and their equivalents are intended to cover such forms or modifications as would fall within the scope and spirit of the inventions.

What is claimed is:

1. A magnetic resonance imaging apparatus comprising sequence controlling circuitry configured:
    to obtain, during a time period after excitation of a first nuclide in a hyperpolarized state but no later than before obtainment of a first magnetic resonance signal from the first nuclide, a second magnetic resonance signal from a second nuclide that is different from the first nuclide and is in a non-hyperpolarized state, by exciting the second nuclide; and
    to control each of gradient magnetic field waveforms so as to cause both a first sum indicating a sum of application amounts of a gradient magnetic field related to the excitation of the second nuclide and a second sum indicating a sum of application amounts of a gradient magnetic field related to the obtainment of the second magnetic resonance signal to be close to zero, no later than before the obtainment of the first magnetic resonance signal.

2. The magnetic resonance imaging apparatus according to claim 1, wherein
    a plurality radio frequency (RF) pulses applied to the first nuclide include a flip pulse and a plurality of flop pulses, and
    the sequence controlling circuitry is configured to obtain the second magnetic resonance signal in a time period between two adjacent flop pulses among the plurality of flop pulses.

3. The magnetic resonance imaging apparatus according to claim 2, wherein the sequence controlling circuitry is configured to excite the second nuclide and to obtain the second magnetic resonance signal in a time period between two applications of a gradient magnetic field related to the application of the plurality of flop pulses.

4. The magnetic resonance imaging apparatus according to claim 2, wherein the sequence controlling circuitry is configured to obtain the first magnetic resonance signal, after one of the plurality of flop pulses that is applied after the obtainment of the second magnetic resonance signal.

5. The magnetic resonance imaging apparatus according to claim 2, wherein the sequence controlling circuitry is configured to apply an RF pulse related to the excitation of the second nuclide, during a time period after the application of the flip pulse but no later than before the application of the flop pulses.

6. The magnetic resonance imaging apparatus according to claim 2, wherein the sequence controlling circuitry is configured to cause the first sum and the second sum to be close to zero no later than before the application of a last one of the plurality of flop pulses.

7. The magnetic resonance imaging apparatus according to claim 1, wherein the first sum and the second sum are both zero.

8. The magnetic resonance imaging apparatus according to claim 1, wherein the following do not overlap with one another: an application time period of a gradient magnetic field at the time of exciting the first nuclide; an application time period of a gradient magnetic field related to the obtainment of the first magnetic resonance signal; an application time period of the gradient magnetic field at the time of exciting the second nuclide; and an application time period of the gradient magnetic field related to the obtainment of the second magnetic resonance signal.

9. The magnetic resonance imaging apparatus according to claim 1, wherein the sequence controlling circuitry is configured to obtain the second magnetic resonance signal multiple times.

10. The magnetic resonance imaging apparatus according to claim 1, wherein the sequence controlling circuitry is configured to simultaneously carry out the excitation of the first nuclide and the excitation of the second nuclide.

11. The magnetic resonance imaging apparatus according to claim 1, wherein, after the obtainment of the first magnetic resonance signal, the sequence controlling circuitry is configured to generate a spoiler pulse related to the obtainment of the second magnetic resonance signal.

12. The magnetic resonance imaging apparatus according to claim 1, wherein the second nuclide is protons.

13. A hyperpolarization signal obtaining method comprising:
- exciting a first nuclide in a hyperpolarized state;
- exciting a second nuclide that is different from the first nuclide and is in a non-hyperpolarized state, during a time period no later than before obtainment of a first magnetic resonance signal from the first nuclide;
- causing a first sum indicating a sum of application amounts of a gradient magnetic field related to the excitation of the second nuclide to be close to zero, no later than before the obtainment of the first magnetic resonance signal;
- obtaining a second magnetic resonance signal from the second nuclide;
- causing a second sum indicating a sum of application amounts of a gradient magnetic field related to the obtainment of the second magnetic resonance signal to be close to zero, no later than before the obtainment of the first magnetic resonance signal; and
- obtaining the first magnetic resonance signal after the second sum is caused to be close to zero.

14. A non-volatile computer-readable storage medium storing therein a hyperpolarization signal obtaining program that causes a computer to realize:
- controlling transmission circuitry so as to excite a first nuclide in a hyperpolarized state;
- controlling the transmission circuitry so as to excite a second nuclide that is different from the first nuclide and is in a non-hyperpolarized state, during a time period no later than before obtainment of a first magnetic resonance signal from the first nuclide;
- controlling a gradient power source so as to cause a first sum indicating a sum of application amounts of a gradient magnetic field related to the excitation of the second nuclide to be close to zero, no later than before the obtainment of the first magnetic resonance signal;
- controlling the gradient power source so as to obtain a second magnetic resonance signal from the second nuclide;
- controlling the gradient power source so as to cause a second sum indicating a sum of application amounts of a gradient magnetic field related to the obtainment of the second magnetic resonance signal to be close to zero, no later than before the obtainment of the first magnetic resonance signal; and
- controlling the gradient power source so as to obtain the first magnetic resonance signal after the second sum is caused to be close to zero.

* * * * *